United States Patent
Aubert et al.

(10) Patent No.: US 7,037,872 B2
(45) Date of Patent: *May 2, 2006

(54) METALLOCENE CATALYSTS CONTAINING A CYCLOPENTADIENYL LIGAND SUBSTITUTED BY A SILOXY OR GERMILOXY GROUP CONTAINING AN OLEFINIC RESIDUE

(75) Inventors: Melanie Aubert, Turku (FI); Carl-Eric Wilen, Espoo (FI)

(73) Assignee: Borealis Technology Oy, Porvoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 10/484,929

(22) PCT Filed: Jul. 24, 2002

(86) PCT No.: PCT/GB02/03383

§ 371 (c)(1),
(2), (4) Date: Apr. 23, 2004

(87) PCT Pub. No.: WO03/010208

PCT Pub. Date: Feb. 6, 2003

(65) Prior Publication Data

US 2004/0198590 A1     Oct. 7, 2004

(30) Foreign Application Priority Data

Jul. 24, 2001    (GB)    ................. 0118010.8

(51) Int. Cl.
*C08F 4/64*   (2006.01)
*C08F 4/74*   (2006.01)
*C08F 4/76*   (2006.01)
*C08F 17/00*  (2006.01)

(52) U.S. Cl. .............. 502/152; 502/103; 502/158; 526/126; 526/127; 526/160; 526/165; 526/172; 556/53

(58) Field of Classification Search ............... 556/53; 502/103, 152, 158; 526/126, 127, 160, 165, 526/172

See application file for complete search history.

(56) References Cited

U.S. PATENT DOCUMENTS

| | | |
|---|---|---|
| 5,071,808 A | 12/1991 | Antberg et al. |
| 5,830,958 A | 11/1998 | Peifer et al. |
| 6,277,778 B1 * | 8/2001 | Leino et al. ............... 502/117 |
| 2004/0152882 A1 | 8/2004 | Ekhom et al. |

FOREIGN PATENT DOCUMENTS

| | | |
|---|---|---|
| EP | 0 574 370 | 12/1993 |
| EP | 0 685 495 | 12/1995 |
| WO | WO 97/27224 | 7/1997 |
| WO | WO 98/46616 | 10/1998 |
| WO | WO 98/52686 | 11/1998 |
| WO | WO 99/14219 | 3/1999 |
| WO | WO 99/29738 | 6/1999 |
| WO | WO 99/43724 | 9/1999 |
| WO | WO 01/53362 | 7/2001 |

* cited by examiner

*Primary Examiner*—Caixia Lu
(74) *Attorney, Agent, or Firm*—Nixon & Vanderhye P.C.

(57) ABSTRACT

The invention relates to a metallocene catalyst in which the metal is coordinated by any $\eta^5$ cyclopentadienyl ligand characterised in that said ligand is directly or indirectly substituted by a pendant siloxy or germyloxy group which contains an olefinic residue.

31 Claims, No Drawings

METALLOCENE CATALYSTS CONTAINING A CYCLOPENTADIENYL LIGAND SUBSTITUTED BY A SILOXY OR GERMILOXY GROUP CONTAINING AN OLEFINIC RESIDUE

This application is the US national phase of international application PCT/GB02/03383 filed 24 Jul. 2002 which designated the U.S. and claims benefit of GB 0118010.8, dated 24 Jul. 2001, the entire content of which is hereby incorporated by reference.

This invention relates to catalysts for olefin polymerisation, in particular to catalysts which comprise a metal bonded to a pentahapto ($\eta^5$) cyclopentadienyl moiety.

In olefin polymerizations, it has long been known to use as a catalyst system the combination of a metallocene procatalyst and an alumoxane co-catalyst or catalyst activator.

By "metallocene" is meant here a metal complex which comprises at least one ligand complexed to a metal and having a hapticity of 2 or greater, for example 2 to 5, especially 5. Metallocenes which comprise one or more pentahapto ($\eta^5$) ligands, for example the cyclopentadienyl ligand, have assumed greatest importance and the subsequent discussion will focus mainly on but is not limited to this subtype of multihapto-containing metal-ligand complexes.

The metallocene may for example be a so-called "open sandwich" or "half sandwich" compound in which the metal is complexed by a single multihapto $\eta^5$ ligand; a "sandwich" compound in which the metal is complexed by 2 or more such ligands; a "handcuff compound" in which the metal is complexed by a bridged bis-multihapto ligand, for example a bis-$\eta^5$-ligand; or a "scorpionate compound" in which the metal is complexed by a multihapto (e.g. $\eta^5$) ligand bridged to a $\eta^1$ (for example a σ-bonded) ligand.

Metallocenes have been much used in the copolymerization of olefins, especially ethylene, propylene, other α-olefins and higher olefins, in the presence of a co-catalyst/catalyst activator such as an alumoxane.

Alumoxanes are compounds with alternating aluminium and oxygen atoms, generally compounds of formula I or II

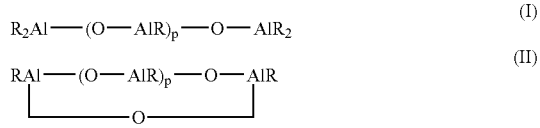

where each R, which may be the same or different, is a $C_{1-10}$ alkyl group, and p is an integer having a value between 0 and 40). These compounds may be prepared by reaction of an aluminium alkyl with water. The production and use of alumoxanes is described in the patent literature, especially the patent applications of Texas Alkyls, Albemarle, Ethyl, Phillips, Akzo Nobel, Exxon, Idemitsu Kosan, Witco, BASF and Mitsui.

Traditionally, the most widely used alumoxane is methylalumoxane (MAO), an alumoxane compound in which the R groups are methyl groups. MAO however is poorly characterised, appears to comprise a range of cage-like structures more complex than the simple linear or cyclic structures of formulae I and II, and is relatively expensive. Accordingly, efforts have been made to use alumoxanes other than MAO. Thus, for example WO98/32775 (Borealis) proposes the use of metallocene procatalysts with alumoxanes in which R is a $C_{2-10}$ alkyl group, e.g. hexaisobutylalumoxane (HIBAO).

The contents of WO98/32775 and all other publications referred to hereafter are hereby incorporated by reference.

Much effort has been expended into the development of improved metallocene-containing catalyst systems on account of the economic importance of olefin polymers. Of particular relevance are the investigations into metallocenes in which the 5-membered cyclopentadienyl ring bonds in a $\eta^5$ fashion to the metal in the complex. For example WO 97/28170 (Borealis) discloses investigations into the substitution of the 5-membered ring of the indenyl moiety with alkoxy, siloxy and other groups.

Research into electronically altered metallocenes, is receiving increasing attention. So too is research into electronically modified cyclopentadienyl or cyclopentadienyl-containing ligands. Exemplary of the cyclopentadienyl-containing ligands are the indenyl, bis(indenyl), indenyloid and bis(indenyloid) ligands. As used herein, the term indenyloid is intended to embrace the general class of anions formed by the deprotonation of any 5,6-fused system whereby to form a cyclopentadienyl $\eta^5$ ligand fused to a 6-membered ring. Indenyl itself may be considered as the parent indenyloid but will be referred to as indenyl here. The fluorenyl ligand is an example of an indenyloid ligand.

For example, it has been reported previously that halogen or alkoxy substitution in the six-membered rings of indenes reduces the activity of the catalyst system and the molecular weight of the produced polymer (Consiglio et al., *Organometallics* 1990, 9, 3098; Collins et al., *Organometallics* 1992, 11, 2115). Bis(indenyl) zirconocenes with 2-amino functionalised ligands have been reported by several groups (Luttikhedde et al., *Organometallics* 1996, 15, 3092; Plenio and Burth, *J. Organomet. Chem.* 1996, 519, 269; Brintzinger et al., *J. Organomet. Chem.* 1996, 520, 63). The bridged complexes show somewhat lower catalytic activities compared with their unsubstituted bis(indenyl) zirconocene analogues.

WO 97/28170 (supra) does in some way address this area. This publication addresses the issue of electronically modifying, by way of substitution, the 5-membered ring of indenyl and indenyloid compounds whereby to produce metallocene compounds in which an oxygen atom is directly bonded to the 2-position of a $\eta^5$ indenyl moiety.

Electronic modification of metallocenes by way of substitution of the 6-membered ring of an indenyl or indenyloid ring by a pendant heteroatom attached group at the 4- or 7-position (i.e. a position adjacent to an atom participating in both the 5- and 6-membered rings) is disclosed in our co-pending International patent application No. PCT/GB02/02853 on 21 Jul. 2002). By pendant is meant that the group is not attached to a second $\eta^5$ group which results in the formation of a "handcuff" metallocene, as discussed above.

In PCT/GB02/02853 supra, we disclose that a number of such compounds, viz metallocenes coordinated by a $\eta^5$ indenyl or indenyloid moiety in which a 6-membered ring is substituted by a siloxy or germyloxy group, exhibit advantageous properties. These complexes, when used as procatalysts in α-olefin polymerisation, allow the production of α-olefin homo or copolymers with notably higher molecular weight than achievable with analogous compounds in which the 6-membered ring is not substituted by a siloxy or germyloxy group. Moreover the activity of these complexes in polymerisations is high, as measured by the quantity of polymer produced per unit time against the quantity of metallocene used; and in copolymerisations, the complexes of the invention result in higher comonomer incorporation than do analogous compounds in which the 6-membered ring is not substituted by a siloxy or germyloxy group.

In metallocene-containing catalyst systems which have been much used in the art, it has often been preferred to introduce the metallocene catalyst or its reaction product with the co-catalyst into the polymerisation reactor in supported form, for example impregnated into a porous particulate support. This is because homogeneous systems when used under slurry polymerisation conditions ae sometimes of limited use since, for example, the polymer produced has low bulk density and particle size and can additionally adhere to the reactor wall during polymerisation. Additionally, these systems often have a short half life. On the other hand, however, the corresponding supported heterogeneous systems can suffer from lower productivity per unit weight of metallocene or compared with corresponding unsupported homogeneous systems.

As used herein the term metallocene catalyst is intended to embrace the actual catalytic species. This may be the metallocene compound itself or a metallocene procatalyst by which term is meant a compound which may be brought into a catalytically active state (e.g. for catalysis of α-olefin polymerization) by reaction with a co-catalyst or catalyst activator, e.g. an aluminium alkyl or other aluminium compound or a boron compound.

In order to try to overcome the disadvantages associated with supported metallocene catalyst systems, and yet retain the advantages inherent to the homogeneous systems, Welch disclosed in U.S. Pat. Nos. 5,240,894, 4,871,705 and 5,106,804 that improved metallocene catalyst systems may be improved by effecting a technique known as prepolymerisation. Welch's systems may be used either with or without a support. However, these techniques did not sufficiently alleviate the problem of polymer adherence, sometimes known as reactor fouling.

Published European patent application No. 0574370 (Fina) discloses metallocene catalyst components which comprise a polymerisable functional group substituent, in particular a long-chain terminal alkene. The particular metallocenes disclosed are substituted isopropyl[(cyclopentadienyl)(fluorenyl)] zirconium dichlorides which contain long-chain terminal alkenes. This alkene may be self-polymerised in the presence of MAO for example, or co-polymerised with propylene whereby to form a prepolymer. It is believed that once the olefinic group is removed from putative intra- or intermolecular n-complexation with the metal ion, catalytic activity increases on account of the increase in accessibility of the catalytic site.

WO 99/29738 (Albermarle) discloses heterogeneous olefin catalysts and catalyst systems devoid of any support. These catalysts were produced by prepolymerising a certain proportion of a vinyl olefin with a Group 4 metallocene alumoxane solution which contains at least one polymerisable olefinic substituent. Such catalysts are referred to as self-supporting catalysts.

Phillips, in WO 99/14219 and U.S. Pat. No. 5,856,547, disclose certain bridged indenyl and indenyloid metallocenes which may contain olefinic groups, optionally attached to the $\eta^5$-ring through silicon. The metallocenes were also prepolymerised with ethylene.

We have now surprisingly found that certain advantages associated with self-supported metallocene catalysts and catalyst systems; and with electronic substitution of cyclopentadienyl-based (particularly indenyl and indenyloid) systems may be combined. We have achieved this by the development of novel cyclopentadienyl-containing (particularly indenyl- and indenyloid-based) ligands which contain one or more germyloxy or silyloxy ligands which ligands carry one or more unsaturated groups capable of reacting to form a desired self-supported catalyst.

Viewed from one aspect, therefore, the present invention provides a metallocene catalyst in which the metal is coordinated by a $\eta^5$ cyclopentadienyl ligand characterised in that said ligand is directly or indirectly substituted by a pendant siloxy or germyloxy group which contains an olefinic residue, e.g. a alkenyl, dienyl or alkynyl residue.

The metal will generally be a transition metal or lanthanide, especially a Group 3 (i.e. including scandium) to Group 7 (i.e. including manganese) transition metal, particularly a Group 4 to 6 metal, in particular Zr, Ti or Hf. For the avoidance of doubt, lanthanide metals herein include lanthanum itself.

Viewed from a further aspect, the invention provides an olefin polymerisation catalyst system comprising or produced by the reaction of:

(i) a metallocene catalyst in which the metal is coordinated by a $\eta^5$ cyclopentadienyl ligand characterised in that said ligand is directly or indirectly substituted by a pendant siloxy or germyloxy group which contains an olefinic residue; and (ii) a cocatalyst/catalyst activator, e.g. an aluminium alkyl compound, in particular an alumoxane, especially an aluminum alkyl compound comprising alkyl groups containing from 1 to 6 carbon atoms.

Alternatively, an aluminum alkyl compound comprising alkyl groups containing at least two carbon atoms may be used.

Viewed from a still further aspect, the invention provides a process for olefin polymerisation comprising polymerising an olefin in the presence of a metallocene catalyst in which the metal is coordinated by a $\eta^5$ cyclopentadienyl ligand characterised in that said ligand is directly or indirectly substituted by a pendant siloxy or germyloxy group which contains an olefinic residue.

Viewed from a yet another aspect, the invention provides a process for the preparation of a metallocene catalyst which comprises metallating a $\eta^5$ cyclopentadienyl ligand with a transition metal or lanthanide, characterised in that said moiety is directly or indirectly substituted by a pendant siloxy or germyloxy group which contains an olefinic residue.

Alternatively, it will be understood that the metallocene catalyst may be produced by the exchange of a metal ion in an existing metallocene for another metal ion through transmetallation.

Viewed from a different aspect, the invention provides an olefin polymer produced in a polymerisation process catalysed by an olefin polymerisation catalyst system comprising or produced by the reaction of (i) a metallocene catalyst in which the metal is coordinated by a $\eta^5$ cyclopentadienyl ligand characterised in that said ligand is directly or indirectly substituted by a pendant siloxy or germyloxy group which contains an olefinic residue; and (ii) a cocatalyst/catalyst initiator, e.g. an aluminium alkyl compound, in particular an alumoxane, especially an aluminum alkyl compound comprising alkyl groups containing from one to six atoms.

Alternatively, an aluminum alkyl compound comprising alkyl groups containing at least two carbon atoms may be used.

Viewed from an alternative aspect, the invention provides the use in olefin polymerisation of a metallocene catalyst in which the metal is coordinated by a $\eta^5$ cyclopentadienyl ligand characterised in that said ligand is directly or indirectly substituted by a pendant siloxy or germyloxy group which contains an olefinic residue.

By directly or indirectly is meant that the pendant siloxy or germyloxy group is either directly bonded to one of the ring carbon atoms of the $\eta^5$ cyclopentadienyl ligand or is attached to one of these atoms, for example, by way of one or more intervening atoms, which may form a fused ring. Thus, for example, the siloxy or germyloxy group may be attached to the six-membered ring of an indenyl (or indenyloid) ring, e.g. either six-membered ring in a fluorenyl ligand, or to a ring fused to any of these rings. It may also (additionally or alternatively) be present on chain L (vide infra).

Thus the catalyst of the invention may for example be a compound of formula (III):

$$(Cp)_p M(X)_m (A)_n \quad (III)$$

in which:

M is a transition metal ion or a lanthanide metal ion;
p is 1 or 2;
m is an integer greater than or equal to 0;
n is an integer greater than or equal to 0;
n+m is equal to the valency of the metal not satisfied by ligand or ligands Cp;
X is a ligand which co-ordinates to M (for example a $\eta^5$ hydrocarbyl, $\eta^1$ hydrocarbyl, halo, hydrocarbyl amino or hydrocarbyl amido ligand);
A is a σ-ligand as defined hereinafter; and
each ligand Cp which may be the same or different is a $\eta^5$ cyclopentadienyl-containing ligand characterised in that at least one of said ligands is directly or indirectly substituted by a pendant siloxy or germyloxy group which contains an olefinic residue, for example $(Cp)_p$ may be one or two ligands "Lig" or "In" as defined hereafter. Hence, where two Cp ligands are present, it is an embodiment of the invention that only one of them carries a pendant siloxy or germyloxy group which contains an olefinic residue.

M in the metallocene catalysts of the invention is preferably a group 4 to 6 transition metal, e.g. a metal selected from Ti, Zr, Hf, V, Nb, Ta, Cr, Mo and W. However, the metal is preferably Cr, Ti, Zr or Hf, particularly Cr if M is liganded by a single multihapto group or Ti, Zr or Hf if M is η-liganded by one or more multihapto groups.

Where p is 2, the two Cp ligands may be connected by one or two, preferably one, bridges L as defined hereinafter.

Useful $\eta^5$ cyclopentadienyl-containing ligands (Cp) according to the invention may be represented by symbol "Lig" wherein Lig consists of a negatively charged cyclopentadienyl-containing moiety of the following formula (IV):

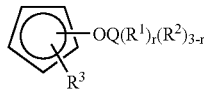

(IV)

(wherein one or more of the ring carbon atoms may be, but are preferably not, replaced by a ring heteroatom;

one or more groups of formula $—OQ(R^1)_r(R^2)_{3-r}$ may be attached to the 5-membered ring shown, either directly or indirectly, preferably directly;

each Q is either a silicon or a germanium atom, preferably a silicon atom;

each r is from 1 to 3, preferably 1;

each $R^1$ which may be the same or different is a $C_{1-20}$ alkenyl group, especially a $C_{1-8}$ alkenyl group which may or may not be cyclic;

each $R^2$ which may be the same or different is a hydrogen or a $C_{1-20}$ hydrocarbyl, especially an alkyl group, especially a $C_{1-8}$ group;

each $R^3$ may be hydrogen or a group bonded through an atom of group 14, 15 or 16 of the periodic table (IUPAC), especially carbon, oxygen, silicon, germanium nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group; optionally two or more $R^3$ groups attached to adjacent ring atoms on the same ring together form a 5- to 8-membered fused ring; and optionally one $R^3$ is -L-Z wherein L is a 1 to 4 atom chain optionally substituted with a group of formula $—OQ(R^1)_r(R^2)_{3-r}$ and Z is a second moiety, which may be the same as or different to said first moiety, preferably of formula (IV) and joined to L through one $R^3$ if present in which L is one and the same chain common to both moieties)

with the proviso that no more than one -L-Z group is present in each ligand Lig.

For the avoidance of doubt, it is hereby stated that one or more than one of any substituent not specifically indicated as being attached to a particular atom in a cyclic structure, for example $R^3$ in moieties of formula (IV), may be present in such a cyclic structure.

In the ligands "Lig" the second moiety Z if present may be any convenient $\eta_5$-cyclopentadienyl ligand. In this way a "handcuff" ligand is provided in which at least one of the cyclopentadienyl ligands is substituted by one or more groups of formula $—OQ(R^1)_r(R^2)_{3-r}$.

Thus particular cyclopentadienyl compounds represented by "Lig" would be those of formula (IVa)

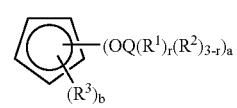

(IVa)

wherein $—OQ(R^1)_r(R^2)_{3-r}$ is directly attached to the cyclopentadienyl ring, Q, $R^1$, $R^2$, $R^3$, r are as hereinbefore defined, a is 1 to 4 (preferably 1 or 2, especially 1), b is 1 to 4 (preferably 1 or 2), the sum of a and b being no more than 5.

Similarly, where one $R_3$ represents L-Z, preferred cyclopentadienyl compounds represented by "Lig" would be those of formula (IVb)

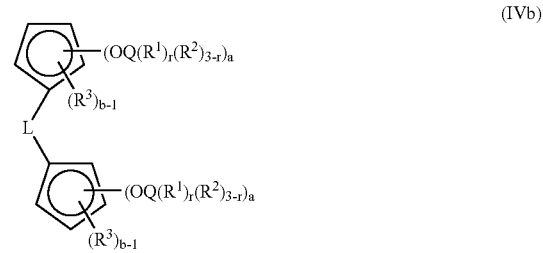

(IVb)

In moieties of formula (V) below, substituent $OQ(R^1)_r(R^2)_{3-r}$ may be present in either or both of the 5- and 6-membered rings shown, bound either directly or indirectly.

Particularly preferred ligands "Lig" may be represented by symbol "In" wherein In consists of a negatively charged indenyl or indenyloid moiety of formula (V)

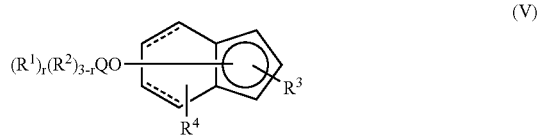
(V)

(wherein one or more of the ring carbon atoms may, but are preferably not, replaced by a ring heteroatom;

either or both of the bonds shown as --- may be present or absent but preferably both are present;

one or more groups of formula $-OQ(R^1)_r(R^2)_{3-r}$ may be attached to either or both of the 5- or 6-membered rings shown, either directly or indirectly, preferably directly;

each Q is either a silicon or a germanium atom, preferably a silicon atom;

each r is from 1 to 3, preferably 1;

each $R^1$ which may be the same or different is a $C_{1-20}$ alkenyl group, especially a $C_{1-8}$ alkenyl group which may or may not be cyclic;

each $R^2$ which may be the same or different is a hydrogen or a $C_{1-20}$ hydrocarbyl, especially an alkyl group, especially a $C_{1-8}$ group;

each $R^3$ or $R^4$ may be hydrogen or a group bonded through an atom of group 14, 15 or 16 of the periodic table (IUPAC), especially carbon, oxygen, silicon, germanium nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group; optionally two or more $R^3$ or $R^4$ groups attached to adjacent ring atoms on the same ring together form a 5- to 8-membered fused ring; and optionally one $R^3$ or $R^4$ is -L-Z wherein L is a 1 to 4 atom chain optionally substituted with a group of formula $-OQ(R^1)_r(R^2)_{3-r}$ and Z is a second moiety, which may be the same as or different to said first moiety, preferably of formula (IV) or formula (V) and joined to L through one bivalent $R^3$ or $R^4$ in which L is one and the same chain common to both moieties)

with the proviso that no more than one -L-Z group is present in each ligand In.

Particularly preferred groups In are therefore of formula (Va)

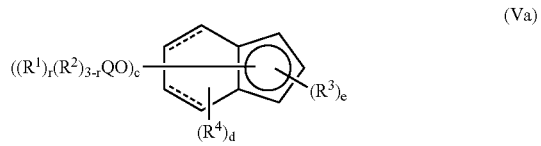
(Va)

wherein $-OQ(R^1)_r(R^2)_{3-r}$ is directly attached to the indenyl ring, Q, $R^1$, $R^2$, $R^3$, $R^4$, r are as hereinbefore defined, c is 1 to 4 (preferably 1 or 2, especially 1), d is 1 to 4, e is 1 to 3, the sum of c, d and e being no more than 7.

Preferably L-Z where present in ligands In is attached to the 5-membered ring, especially at the 1- or 3-positions or less preferably to the 6-membered ring at the 4- or 7 positions. [Throughout this specification the numbering of carbon atoms is derived from the IUPAC numbering scheme for the indenyl ring.]

The ligands in themselves are novel and form a further aspect of the invention. Viewed from this aspect, therefore, there is provided a ligand Lig which consists of negatively charged cyclopentadienyl-containing moiety of the following formula (IV):

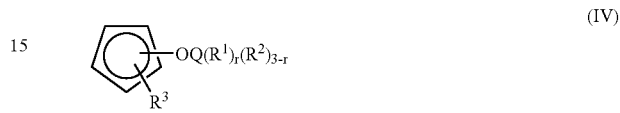
(IV)

(wherein one or more of the ring carbon atoms may, but are preferably not, replaced by a ring heteroatom;

one or more groups of formula $-OQ(R^1)_r(R^2)_{3-r}$ may be attached to the 5-membered ring shown, either directly or indirectly, preferably directly;

each Q is either a silicon or a germanium atom, preferably a silicon atom;

each r is from 1 to 3, preferably 1;

each $R^1$ which may be the same or different is a $C_{1-20}$ alkenyl group, especially a $C_{1-8}$ alkenyl group which may or may not be cyclic;

each $R^2$ which may be the same or different is a hydrogen or a $C_{1-20}$ hydrocarbyl, especially an alkyl group, especially a $C_{1-8}$ group;

each $R^3$ may be hydrogen or a group bonded through an atom of group 14, 15 or 16 of the periodic table (IUPAC), especially carbon, oxygen, silicon, germanium nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group; optionally two or more $R^3$ groups attached to adjacent ring atoms on the same ring together form a 5- to 8-membered fused ring; and optionally one $R^3$ is -L-Z wherein L is a 1 to 4 atom chain optionally substituted with a group of formula $-OQ(R^1)_r(R^2)_{3-r}$ and Z is a second moiety, which may be the same as or different to said first moiety, preferably of formula (IV) and joined to L through one $R^3$ if present in which L is one and the same chain common to both moieties)

with the proviso that no more than one -L-Z group is present in each ligand Lig) and salts and complexes thereof.

There is also provided a ligand In wherein In consists of a negatively charged indenyl or indenyloid moiety of formula (V)

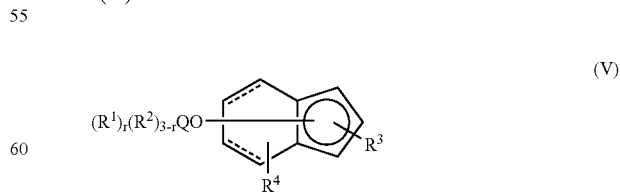
(V)

(wherein one or more of the ring carbon atoms may, but are preferably not, replaced by a ring heteroatom;

either or both of the bonds shown as --- may be present or absent but preferably both are present;

one or more groups of formula —OQ($R^1$)$_r$($R^2$)$_{3-r}$ may be attached to either or both of the 5- or 6-membered rings shown, either directly or indirectly, preferably directly;

each Q is either a silicon or a germanium atom, preferably a silicon atom;

each r is from 1 to 3, preferably 1;

each $R^1$ which may be the same or different is a $C_{1-20}$ alkenyl group, especially a $C_{1-8}$ alkenyl group which may or may not be cyclic;

each $R^2$ which may be the same or different is a hydrogen or a $C_{1-20}$ hydrocarbyl, especially an alkyl group, especially a $C_{1-8}$ group;

each $R^3$ or $R^4$ may be hydrogen or a group bonded through an atom of group 14, 15 or 16 of the periodic table (IUPAC), especially carbon, oxygen, silicon, germanium nitrogen or sulfur, e.g. $C_{1-20}$ hydrocarbyl, hydrocarbyl siloxy, hydrocarbyloxy, hydrocarbylgermyloxy, hydrocarbyl silyl or hydrocarbylgermyl group particularly an oxygen-, silicon-, germanium- or sulfur-attached hydrocarbyl group; optionally two or more $R^3$ or $R^4$ groups attached to adjacent ring atoms on the same ring together form a 5- to 8-membered fused ring; and optionally one $R^3$ or $R^4$ is -L-Z wherein L is a 1 to 4 atom chain optionally substituted with a group of formula —OQ($R^1$)$_r$($R^2$)$_{3-r}$ and Z is a second moiety, which may be the same as or different to said first moiety, preferably of formula (IV) or formula (V) and joined to L through one bivalent $R^3$ or $R^4$ in which L is one and the same chain common to both moieties)

with the proviso that no more than one -L-Z group is present in each ligand In) and salts and complexes thereof.

In Ligands "In" which contain one or two moieties of formula (V), one or more groups of formula OQ($R^1$)$_r$($R^2$)$_{3-r}$ may be present in either the 6- or the 5-membered rings in either or both of these moieties. Preferably, such a substituent is present in the 5-membered ring.

Also, in ligands which contain one moiety of formula (V), where L is present, it may be linked to either the 5- or the 6-membered ring; or, if two moieties of formula (V) are present, L may be linked to two 5-membered rings or to two 6-membered rings.

In ligands where L is present, L may be substituted with one or more groups of formula OQ($R^1$)$_r$($R^2$)$_{3-r}$. Such substitution is an example of indirect substitution of moieties (IV) and (V).

By fused or non-fused is meant that the ligand may have two carbon or heteroatoms also forming part of an additional ring which may itself by fused or an optionally substituted carbocyclic or heterocyclic ring etc. For example the fluorenyl ring is embraced by this invention.

By homo- or heterocyclic is meant that any moiety of formula (IV) or (V) may have only carbon ring atoms (i.e. homo or isocyclic) or may have ring atoms other than carbon (heterocyclic). Such ring heteroatoms may for example be, independently from each other, N, S, Se, O, P, B or Si.

Preferred ligands Lig are those in which one group $R^3$ is of formula -L-Z. Preferred ligands In are those in which one group $R^3$ or $R^4$ is of formula -L-Z, preferably $R^3$. Particularly preferred are those in which -L-Z is present at the 1-position in moieties of formula (V) and/or in which Z is another group of formula (IV) or (V). For "In" ligands $R^3$ and $R^4$ groups which do not represent a group L-Z are preferably hydrogen atoms. For cyclopentadienyl ligands $R^3$ and $R^4$ groups which do not represent a group L-Z are preferably hydrogen atoms or may also preferably represent $C_{1-6}$-alkyl groups, e.g. methyl. In such a scenario 1 or 2 such $C_{1-6}$-alkyl groups are preferably present.

In ligands Lig and In, including those preferred types described herein, L is preferably of formula $(C(R^3)_2)_q$ or $Si(R_3)_2$ in which q is 1 or 2 and $R^3$ is as hereinbefore defined (but may not represent a group L-Z) but is preferably hydrogen or a $C_{1-20}$-hydrocarbyl group. Ideally the bridge L is an ethylene, —Si(CH$_3$)[Si(CH$_3$)$_3$]—, —(SiMe$_2$)$_2$— or dimethylsilylene bridge. Alternatively, these L groups may of course contain one or more groups of formula OQ($R^1$)$_r$($R^2$)$_{3-r}$.

In at least one of and preferably in all of the group or groups of formula OQ($R^1$)$_r$($R^2$)$_{3-r}$, $R^1$ where acyclic has a terminal alkenyl group.

Further preferred catalysts of the invention are therefore of formula

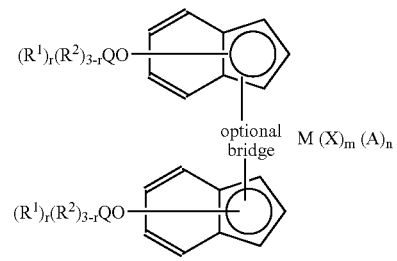

wherein ($R^1$)$_r$($R^2$)$_{3-r}$QO, M, X, A, m and n are as hereinbefore defined and the bridge, if present is L, preferably bridging the indenyl groups at the 1-position; or of formula

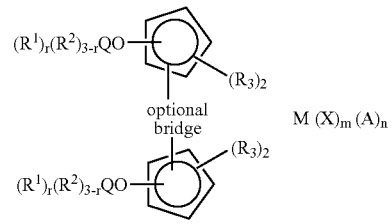

wherein ($R^1$)$_r$($R^2$)$_{3-r}$QO, M, X, A, m and n are as hereinbefore defined and the bridge, if present, is L, each $R_3$ being hydrogen or a $C_{1-6}$ alkyl group.

Compounds of formula (III) are preferably of formula (Cp)M(A)$_n$ wherein M, A and n are as hereinbefore defined; and (Cp) is a ligand Lig in which one group $R^3$ is -L-Z; or a ligand "In" in which one group $R^3$ or one group $R^4$ is -L-Z, where L is preferably of formula $C(R^3)_2$, $((CR^3)_2)_2$ or $Si(R_3)_2$ in which each $R^3$ may be the same or different and is as hereinbefore defined but is preferably hydrogen, a hydrocarbyl silyl group or a hydrocarbyl group. An example of such a suitable L group is —Si(CH$_3$)[Si(CH$_3$)$_3$]—. Z is a second moiety preferably of formula (IV) or (V) which may or may not be the same as the first moiety. In one embodiment Z is identical to the first moiety apart from the substitution of the group hydrogen for $R^1$)$_r$($R^2$)$_{3-r}$QO.

In the group ($R^1$)$_r$($R^2$)$_{3-r}$QO, Q is preferably silicon. $R^1$ is preferably a $C_{1-16}$ alkenyl group, especially a $C_{1-8}$ alkenyl group. Where the alkenyl group is acyclic the double bond is preferably found in the terminal position. Particular groups of interest include n-propenyl, n-butenyl, n-hexenyl, n-heptenyl and n-octenyl. Cyclic alkenyl groups include cyclohexenyl, norbornenyl (bicyclo[2.2.1]hepta-2-ene) or bicyclo[2.2.2]hepta-2-ene. It is also within the scope of the invention for the $R_1$ group to represent a diene, e.g. a $C_{1-10}$ linear diene such as butadiene. $R_2$ is preferably a $C_{1-16}$ alkyl group, e.g. $C_{1-10}$ alkyl group. Specific $R_2$ groups are therefore methyl, ethyl, propyl, isopropyl, butyl, tertbutyl etc. Isopropyl is especially preferred and when two $R_2$ groups are present it is preferred if these are the same.

Examples of suitable $(R^1)_r(R^2)_{3-r}QO$ groups wherein Q=Si in the metallocene procatalysts of the invention therefore include:

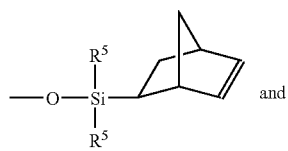 and

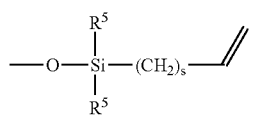

wherein s is 1 to 18, preferably 1 to 6 and each $R^5$ is independently selected from the group comprising $C_{1-6}$ alkyl groups, e.g. methyl, ethyl or isopropyl etc. Preferably both $R^5$ groups are the same.

The $(R^1)_r(R^2)_{3-r}QO$ group may be bound to any available group on the cyclopentadienyl or indenyl ring, preferably directly. Where the $\eta^5$-ligand is an indenyl, it is preferred if the $(R^1)_r(R^2)_{3-r}QO$ group binds to the 2 or 4 position of the indenyl, the bridge (if present) being attached via the 1-position. Alternatively the $(R^1)_r(R^2)_{3-r}QO$ group may be bound to the 3-position of the indenyl group or the 1-position if no bridge is present.

Where the $\eta^5$-ligand comprises a bridged cyclopentadienyl group it is preferred if the bridge and $(R^1)_r(R^2)_{3-r}QO$ group are on adjacent carbon atoms.

Thus typical examples of ligands Lig and In include the following bridged bis indenes:

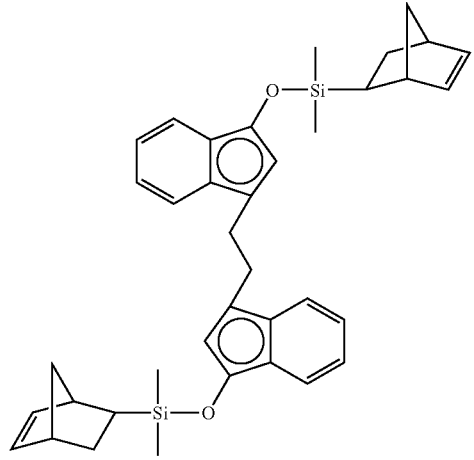

-continued

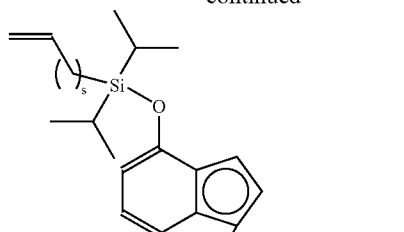

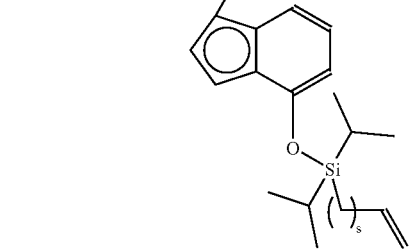

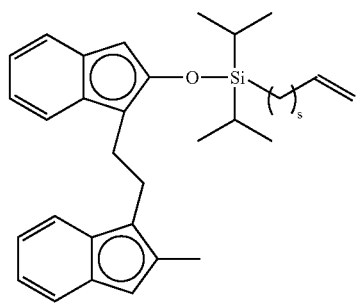

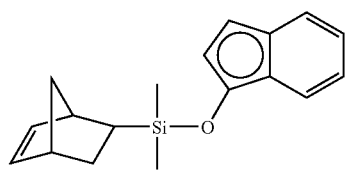

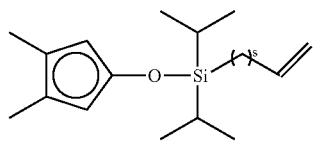

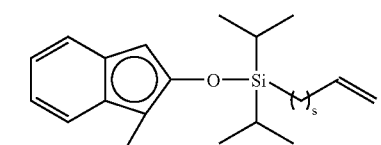

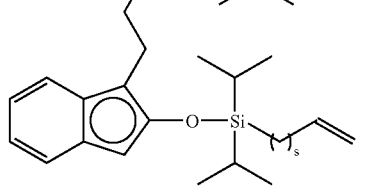

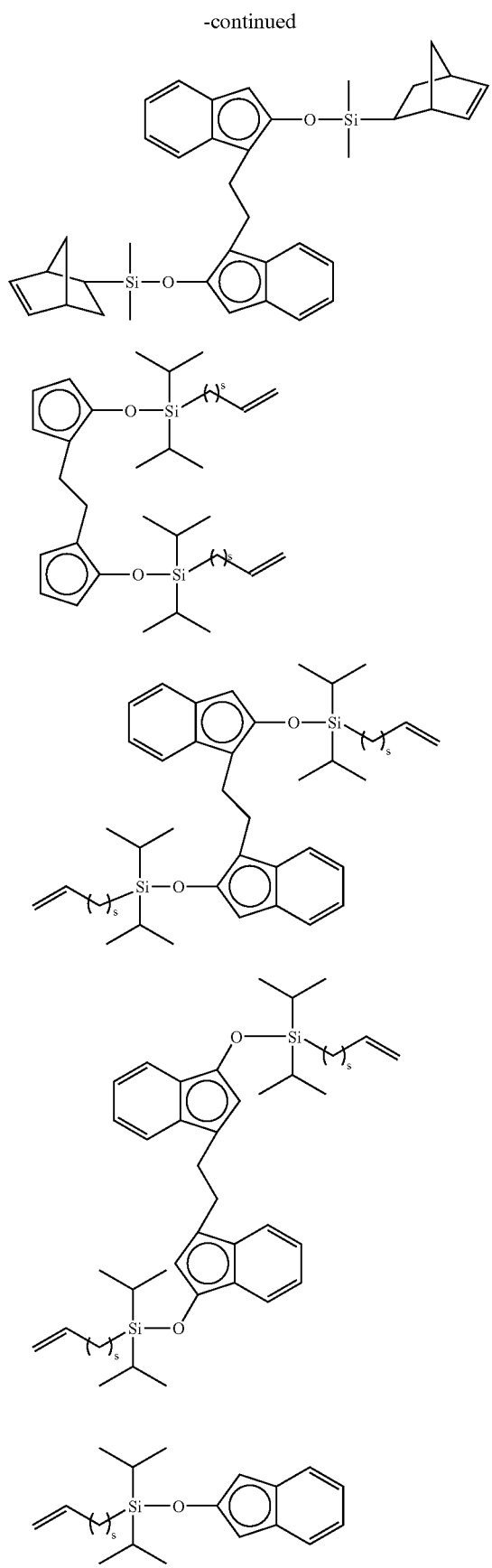
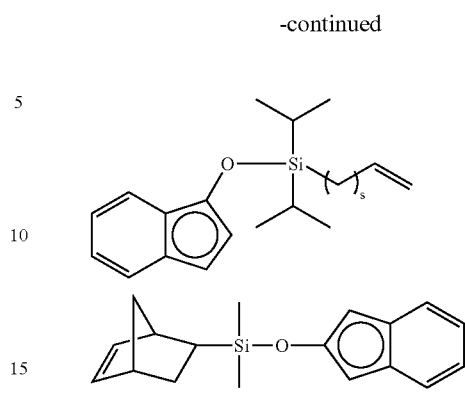
Typical examples of the metallocene catalysts of the invention thus include:
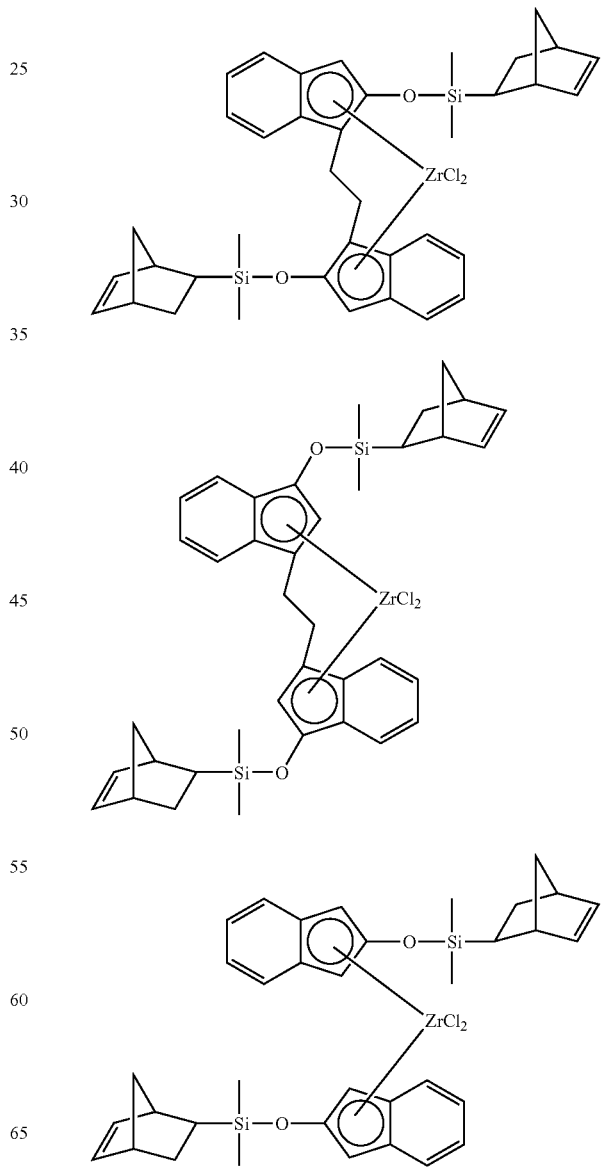

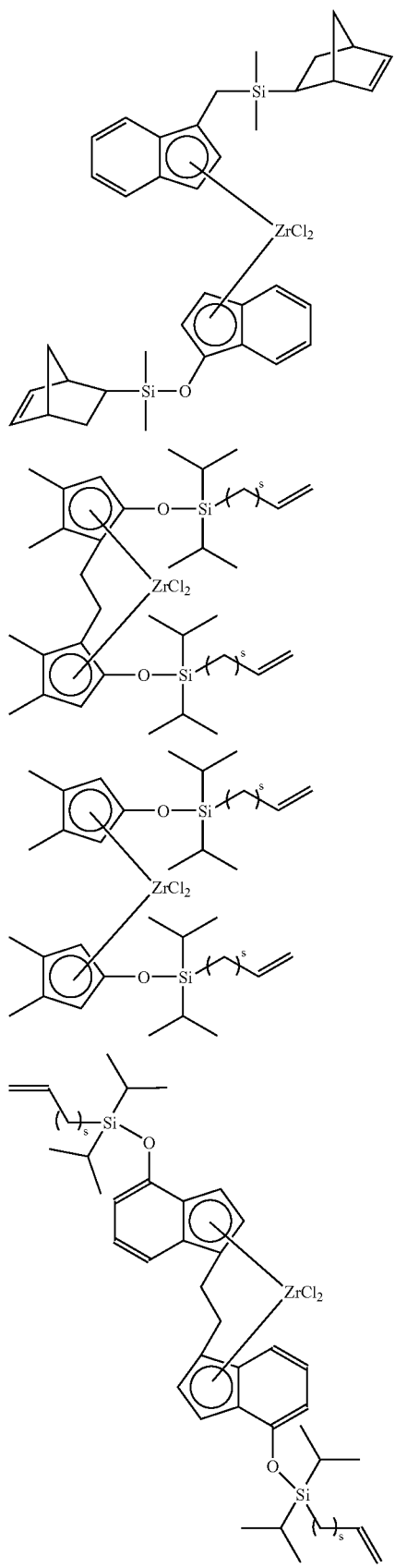
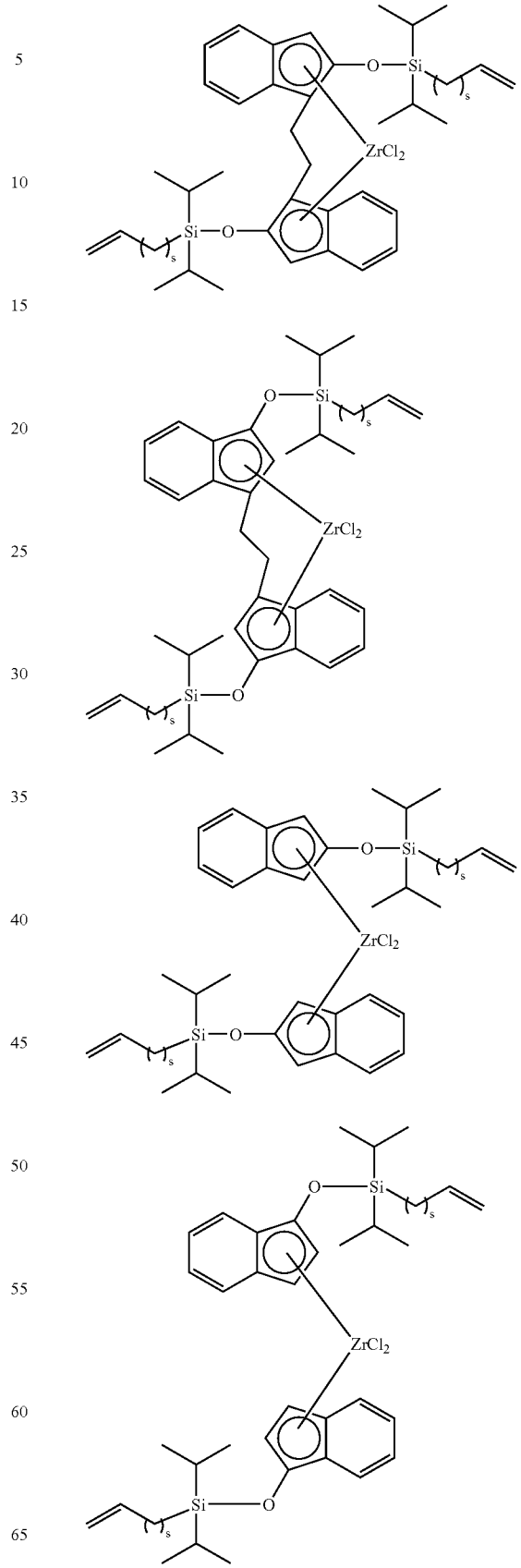

-continued

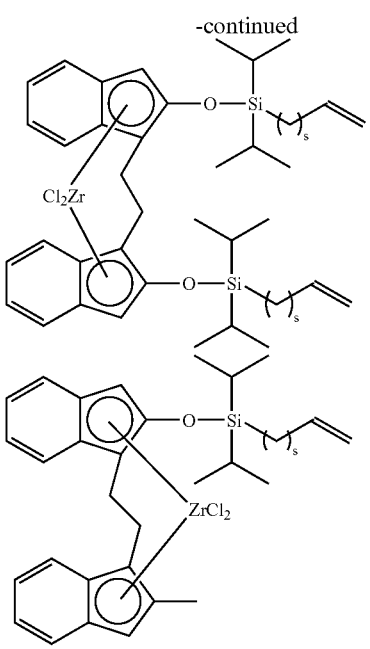

The skilled man will readily understand that both rac and meso compounds may be used according to the present invention. Thus meso equivalents of the each of the above rac catalysts above are envisaged according to the various aspects of the invention.

Examples of particular further η-ligands are well known from the technical and patent literature relating to metallocene olefin polymerization catalysts, e.g. EP-A-35242 (BASF), EP-A-129368 (Exxon), EP-A-206794 (Exxon), WO 97/28170 (Borealis), EP-A-318048, EP-A-643084, EP-A-69951, EP-A-410734, EP-A-128045, EP-B-35242 (BASF), EP-B-129368 (Exxon) and EP-B-206794 (Exxon). These include
cyclopentadienyl,
indenyl,
fluorenyl,
octahydrofluorenyl,
methylcyclopentadienyl,
1,2-dimethylcyclopentadienyl,
pentamethylcyclopentadienyl,
pentyl-cyclopentadienyl,
2-dimethyl, tertbutylsiloxy-inden-1-yl,
n-butylcyclopentadienyl,
1,3-dimethylcyclopentadienyl,
4,7-dimethylindenyl,
1,-ethyl-2-methylcyclopentadienyl,
tetrahydroindenyl, and
methoxycyclopentadienyl.

By a σ-ligand moiety is meant a group bonded to the metal at one or more places via a single atom, eg a hydrogen, halogen, silicon, carbon, oxygen, sulphur or nitrogen atom. Examples of such ligands include:
halogenides (e.g. chloride and fluoride),
hydrogen,
triC$_{1-12}$ hydrocarbyl-silyl or -siloxy(e.g. trimethylsilyl),
triC$_{1-6}$ hydrocarbylphosphimido (e.g. triisopropylphosphimido),
C$_{1-12}$ hydrocarbyl or hydrocarbyloxy (e.g. methyl, ethyl, phenyl, benzyl and methoxy),
diC$_{1-6}$ hydrocarbylamido (e.g. dimethylamido and diethylamido), and
5 to 7 ring membered heterocyclyl (e.g. pyrrolyl, furanyl and pyrrolidinyl).

The olefin-containing siloxy or germyloxy cyclopentadienyl-containing ligands used according to the various aspects of the invention may be prepared by any convenient means. For example, to prepare a suitable cyclopentadienyl ligand for use in preparing a metallocene catalyst of the invention, an appropriate compound of formula $(R^1)_r(R^2)_{3-r}$QHal (wherein R$^1$ R$^2$ and Q are as defined above and Hal is a halide, for example chloride, bromide or iodide (chloride being preferred)) may be reacted with triflic acid in the absence of solvent at a temperature of from 60 to 140° C., e.g. 70–110° C., for example about 80° C. to afford a corresponding silyl or germyl triflate of formula $F_3SO_2Q(R^1)_r(R^2)_{3-r}$. After purification (e.g. by distillation), the triflate may be reacted with a cyclopentenone, e.g. a cyclopent-2-enone substituted with group or groups R$^3$ (as hereinbefore defined) as appropriate with a suitable base such as triethylamine, imidazole or 1,8-diazo-bicyclo[5,6,0]undec-7-ene (DBU) may be employed in a hydrocarbon solvent such as pentane to afford a siloxy or germyloxy cyclopent-1,4-diene.

The starting materials of formula $(R^1)_r(R^2)_{3-r}$QHal may be prepared by a reaction between one or more equivalents of a compound of formula R$^6$MgBr (wherein R$^6$ may be either R$^1$ or R$^2$) with a compound equivalent to $(R^1)_r(R^2)_{3-r}$QHal but in which one or more R$^1$ and/or R$^2$ groups are replaced by further ligands Hal. Thus for example, 3-butenyldiisopropylchlorosilane may be produced by the reaction between diisopropyldichloro-silane and one equivalent of 3-butenyl magnesium chloride; or a compound of formula (VII) may be produced from a compound of formula (VI) by the reaction shown below:

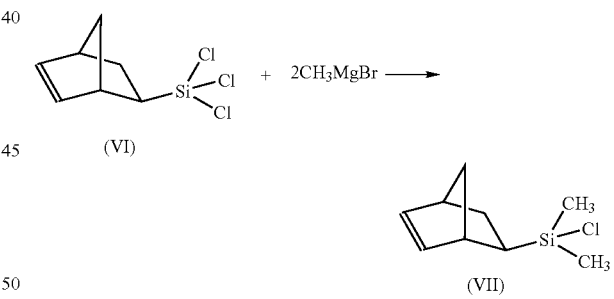

Where polycyclic cyclopentadienyl ligands are desired, these may be prepared by way of a corresponding indene or indenoid or analogue thereof (for example a 9-fluorenone) which is directly or indirectly substituted with a hydroxyl group may be used as a starting material. Such compounds (e.g. 2-hydroxy-9-fluorenone and 4- and 5-hydroxy-indanone, which may be purchased from Aldrich) are commercially available. Alternatively, appropriate hydroxy-substituted indenes or other polycyclic structures containing the indene skeleton and with one or more appropriate hydroxyl groups, may be used as starting materials.

These starting materials may be reacted with a compound of formula $(R^1)_r(R^2)_{3-r}$QHal wherein R$^1$, R$^2$, Q and Hal are as defined above in a suitable solvent, for example N,N-dimethyl formamide (DMF) or dichloromethane.

Covalent catalysis may be used to assist in such reactions, e.g. effective quantities of triethylamine, (DBU) or imidazole may be employed.

Where the starting materials comprise more than one hydroxyl group, such reactions permit the formation of mono- or bis-substituted siloxy or germyloxy compounds. Moreover, it is also possible to react an appropriate starting indanone, for example 4-hydroxy-indan-1-one with two equivalents of compound of formula $(R^1)_r(R^2)_{3-r}QHal$, which may or may not be the same, to afford the corresponding bis ether of 1,4-dihydroxy-ind-1-ene through trapping of the enol tautomer.

The appropriate siloxy or germyloxy compounds may then be converted by, for example, a two-step process involving converting the indanone into a hydrazone (e.g. by reaction with tosyl hydrazine), in the presence of an effective amount of sulfuric acid in methanol; followed by reaction of the so-formed hydrazone with an appropriate base, e.g. an organolithium compound, such as methyllithium or butyllithium. The parent reaction here is commonly known as the Shapiro reaction. Particular bases of use in this regard include t-BuLi, n-BuLi, lithium diisopropylamide, t-BuOK, trialkylamines, dialkyl-magnesium, alkylmagnesium chloride, alkyl CuLi and dialkyl zinc which may be used in conjunction with a suitable solvent. If necessary, a donor such as dimethoxyethane may be added to the reaction medium containing the hydrazone prior to addition of the base.

Alternatively, the keto group in the indanone may simply be reduced under standard conditions (e.g. sodium borohydride in methanol and/or tetrahydrofuran (THF)) followed by dehydration to form the desired indene or indene skeleton-containing compound.

If the formation of a bisindenyl or bisindenyloid ligand (i.e. a "handcuff" ligand as herein before defined) is desirable, two equivalents (which may or may not be the same) of a siloxy or germyloxy substituted cyclopenta-1,4-diene, 1H- or 3H-indene etc may be reacted with an appropriate base, e.g. an organolithium compound, such as methyllithium or butyllithium. Particular bases and solvents of use in this regard are as hereinbefore defined. If necessary, a donor such as dimethoxyethane may be added to the reaction medium containing the appropriate siloxy or germyloxy substituted cyclopenta-1,4-diene, 1H- or 3H-indene etc, prior to addition of the base.

The anion or anions, as appropriate, may be reacted with a molecule of formula $LG_1$-L-$LG_2$ (wherein L is as hereinbefore defined and $LG_1$ and $LG_2$ represent any appropriate leaving groups which may or may not be the same, for example bromide, tosyl, chloride etc., whereby to form the desired bisindenyl ligand. Alternatively, a "handcuff" ligand may be formed by a two step process in which one equivalent of a first cyclopentadienyl, indenyl, or indenyloidyl anion is reacted with one equivalent of $LG_1$-L-$LG_2$ and the resultant cyclopentadiene etc substituted with -L-$LG_2$ may be reacted with a second molecule anion whereby to form the desired bridged bis ligand.

Alternatively, where a substituent $R^4$ in moieties of formula (V) is of formula -L-Z, indenyl(oid) to indenyl(oid) bridging may be achieved using the methods disclosed in WO96/38458).

Formation of the desired metallocene is effected by reacting the desired ligand with an appropriate quantity of base, e.g. an organolithium compound, such as methyllithium or butyllithium (i.e. where formation of a mono $\eta^5$ ligand is desired, one equivalent of base is used and where a bisindenyl ligand is being used (i.e. a bis $\eta^5$ ligand) two equivalents of base may be used. Particular bases and solvents of use in this regard are as hereinbefore defined. If necessary, a donor such as dimethoxyethane may be added to the reaction medium containing the appropriate 1H or 3H indene etc prior to addition of the base.

The ligand can be metallated conventionally, e.g. by reaction with a halide of the metal M, preferably in an organic solvent, e.g. a hydrocarbon or a hydrocarbon/ether mixture. Bridged siloxy- or germyloxy cyclopentadienyl ligands may be constructed by reacting a siloxy- or germyloxy monocyclopentadienyl ligand with a bridging agent (e.g. $Si(CH_3)_2Cl_2$) or with a bridging agent and a further $\eta$-ligand (e.g. a different cyclopentadienyl ligand or with an indenyl, fluorenyl, etc ligand).

An alternative approach to the complexes is also envisaged where the siloxycyclopentadiene is reacted with $Zr(NMe_2)_4$ or $Zr(CH_2Ph)_4$ followed by $Me_3SiCl$ to yield the complex directly. Also, trimethylsilyl (siloxy) cyclopentadiene reacts with $ZrCl_4$ to afford the complex directly.

σ-ligands other than chlorine may be introduced by displacement of chlorine from an η-ligand metal chloride by reaction with appropriate nucleophilic reagent (e.g. methyl lithium or methylmagnesium chloride) or using, instead of a metal halide, a reagent such as tetrakisdimethylamidotitanium or metal compounds with mixed chloro and dimethylamido ligands.

As mentioned above, the olefin polymerisation catalyst system of the invention comprises (i) a metallocene catalyst in which the metal is coordinated by a $\eta^5$ cyclopentadienyl ligand characterised in that said ligand is directly or indirectly substituted by a pendant siloxy or germyloxy group which contains an olefinic residue.

While the aluminium alkyl compound may be an aluminium trialkyl (e.g. triethylaluminium (TEA)) or an aluminium dialkyl halide (e.g. diethyl aluminium chloride (DEAC)), it is preferably an alumoxane, particularly an alumoxane such as MAO; or an isobutylalumoxane, e.g. TIBAO (tetraisobutylalumoxane) or HIBAO (hexaisobutylalumoxane). Alternatively, however, the alkylated (e.g. methylated) metallocene catalysts of the invention may be used with other cocatalysts, e.g. boron compounds such as $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4{}^{2-}$.

However, when the metal in the catalyst is a group 3 transition metal, i.e. Sc, Y, La or Ac, no co-activator is required since such catalyst species are already in an active form, e.g. compounds of formula $Lig_2ScH$ wherein Lig is as hereinbefore defined.

The metallocene catalyst and cocatalyst may be introduced into the polymerization reactor separately or together or, more preferably they are pre-reacted and their reaction product is introduced into the polymerization reactor.

As made clear above, the advantage of the invention lies partly in the production of self-supporting metallocene catalysts. Thus the catalyst, catalyst/cocatalyst mixture or a catalyst/cocatalyst reaction product may be used in unsupported form, i.e. metallocene and MAO are used without an actual carrier material conventionally used in the field.

Self-supporting catalysts may be produced by self-polymerisation of the catalysts themselves, i.e by polymerisation of the olefinic residues attached to the siloxy or germyloxy group(s) according to the methods disclosed in EP 574 370 supra; by pre-polymerisation between the olefin-containing catalyst according to the methods disclosed in EP 574 370, supra or EP 685 495, WO99/43724, or WO99/14219 (all Phillips); or by preinitiation as disclosed in WO97/27224 (Borealis) in which the metallocene is reacted with 0.05–500 moles of an unsaturated organic compound/mole of transition metal compound. A degree of self-polymerisation may of course occur during prepolymerisation and preinitiation processes. Of these methods whereby self-supported catalyst systems may be produced, prepolymerisation is preferred.

In any of the polymerisation processes of the invention, e.g. the polymerisation of the olefin itself, or during the prepolymerisation or preinitiation polymerisation processes, the processes may be conducted at temperatures of from −10 to 300° C. and olefin (e.g ethylene) pressures of from 0.01 to 3000 bar.

Whilst the utility of the metallocene catalyst or its reaction product with the cocatalyst in self-supported catalytic systems is preferred, the catalysts described herein may alternatively, but less preferably be introduced into the polymerization reactor in supported form, e.g. impregnated into a porous particulate support.

The particulate support material if used is an inorganic material or, preferably, an organic material, e.g. a polymer (such as for example polyethylene, polypropylene, an ethylene-propylene copolymer, another polyolefin or polystyrene or a combination thereof). Such polymeric supports may be formed by precipitating a polymer or by a prepolymerization, e.g. of monomers used in the polymerization for which the catalyst is intended. However, the support is especially preferably a metal or metalloid oxide such as silica, alumina or zirconia or a mixed oxide such as silica-alumina, in particular silica, alumina or silica-alumina.

Especially preferably the support is a porous material so that the metallocene may be loaded into the pores of the support, e.g. using a process analogous to those described in WO94/14856 (Mobil), WO95/12622 (Borealis) and WO96/00243 (Exxon). The particle size is not critical but is preferably in the range 5 to 200 μm, more preferably 20 to 80 μm.

The active metal (i.e. the metal of the catalyst) is preferably loaded onto the support material at from 0.1 to 4%, preferably 0.5 to 3.0%, especially 1.0 to 2.0%, by weight metal relative to the dry weight of the support material.

Where a cocatalyst or catalyst activator is used, it is preferably used in a mole ratio to the metallocene of from 0.1:1 to 10000:1. More particularly, where an alumoxane cocatalyst is used, then for an unsupported catalyst the aluminium:metallocene metal (M) molar ratio is conveniently 2:1 to 10000:1, preferably 50:1 to 1000:1. Where the catalyst is supported the Al:M molar ratio is conveniently 2:1 to 10000:1 preferably 50:1 to 400:1. Where a borane cocatalyst (catalyst activator) is used, the B:M molar ratio is conveniently 2:1 to 1:2, preferably 9:10 to 10:9, especially 1:1. When a neutral triarylboron type cocatalyst is used the B:M molar ratio is typically 1:2 to 500:1, however some aluminium alkyl would normally also be used. When using ionic tetraaryl borate compounds, it is preferred to use carbonium rather than ammonium counterions or to use B:M molar ratio 1:1.

The olefin polymerized in the method of the invention is preferably ethylene or an alpha-olefin or a mixture of ethylene and an α-olefin or a mixture of alpha olefins, for example $C_{2-20}$ olefins, e.g. ethylene, propene, but-1-ene, hex-1-ene, 4-methyl-pent-1-ene, oct-1-ene etc. The olefins polymerized in the method of the invention may include any compound which includes unsaturated polymerizable groups. Thus for example unsaturated compounds, such as $C_{6-20}$ olefins (including cyclic and polycyclic olefins (e.g. norbornene)), and polyenes, especially $C_{6-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α,ω linear dienes such as 1,5-hexadiene, 1,6-heptadiene, 1,8-nonadiene, 1,9-decadiene, etc.

In general, where the polymer being produced is a homopolymer it will preferably be polyethylene or polypropylene. Where the polymer being produced is a copolymer it will likewise preferably be an ethylene or propylene copolymer with ethylene or propylene making up the major proportion (by number and more preferably by weight) of the monomer residues. Comonomers, such as $C_{4-6}$ alkenes, will generally be incorporated to contribute to the mechanical strength of the polymer product.

Usually metallocene catalysts yield relatively narrow molecular weight distribution polymers; however, if desired, the nature of the monomer/monomer mixture and the polymerization conditions may be changed during the polymerization process so as to produce a broad bimodal or multimodal molecular weight distribution (MWD) in the final polymer product. In such a broad MWD product, the higher molecular weight component contributes to the strength of the end product while the lower molecular weight component contributes to the processability of the product, e.g. enabling the product to be used in extrusion and blow moulding processes, for example for the preparation of tubes, pipes, containers, etc.

A multimodal MWD can be produced using a catalyst material with two or more different types of active polymerization sites, e.g. with one such site provided by the metallocene on the support and further sites being provided by further catalysts, e.g. Ziegler catalysts, other metallocenes, etc. included in the catalyst material.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase.

For slurry reactors, the reaction temperature will generally be in the range 60 to 110° C. (e.g. 85–110° C. or 80 to 110° C.), the reactor pressure will generally be in the range 5 to 80 bar (e.g. 50–65 bar), and the residence time will generally be in the range 0.3 to 5 hours (e.g. 0.5 to 2 hours). The diluent, if used, will generally be an aliphatic hydrocarbon having a boiling point in the range −70 to +100° C. In such reactors, polymerization may if desired be effected under supercritical conditions.

For gas phase reactors, the reaction temperature used will generally be in the range 60 to 115° C. (e.g. 70 to 110° C.), the reactor pressure will generally be in the range 10 to 25 bar, and the residence time will generally be 1 to 8 hours. The gas used will commonly be a non-reactive gas such as nitrogen together with monomer (e.g. ethylene).

For solution phase reactors, the reaction temperature used will generally be in the range 130 to 270° C., the reactor pressure will generally be in the range 20 to 400 bar and the residence time will generally be in the range 0.005 to 1 hour. The solvent used will commonly be a hydrocarbon with a boiling point in the range 80–200° C.

Generally the quantity of catalyst used will depend upon the nature of the catalyst, the reactor types and conditions and the properties desired for the polymer product. Conventional catalyst quantities, such as described in the publications referred to herein, may be used.

The invention will now be illustrated by reference to the following non-limiting Examples:

Ligand and Complex Synthesis

All operations are carried out under an argon or nitrogen atmosphere using standard Schlenk, vacuum and drybox techniques. Diethyl ether, tetrahydrofuran (THF) and benzene solvents were dried with potassium benzophenone ketyl and distilled under argon prior to use. Other solvents were dried using 13X+13 Å molecular sieves. All other chemicals were used as commercially available.

NMR spectra were recorded using a JEOL JNM-EX270 MHz FT-NMR spectrometer with tetramethylsilane (TMS) as an internal reference.

Direct inlet mass spectra were recorded using a VG TRIO 2 quadruple mass spectrometer in electron impact ionization mode (70 eV).

GC-MS analysis was performed using a Hewlett Packard 6890/5973 Mass Selective Detector in electron impact ionization mode (70 eV), equipped with a silica capillary column (30 m×0.25 mm i.d).

[Ethylenebis(2-(4-butenyldiisopropylsiloxy)-1-indenyl)]zirconium dichloride (4)

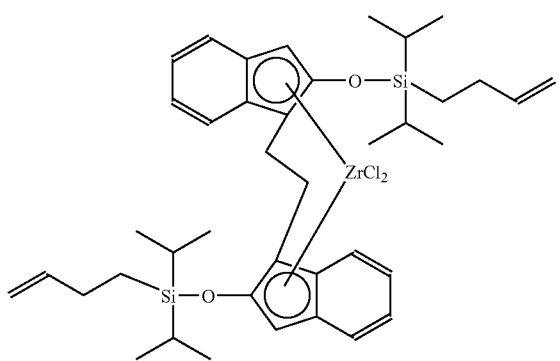

(4)

Synthesis of (4-butenyldiisopropylchloro)silane (1)

To a suspension of magnesium turnings (2.65 g, 0.11 mol) in THF (50 ml) was added dropwise 4-bromo-1-butene (15 g, 0.11 mol) and the reaction mixture stirred for 12 hours. The solution was then cooled to −10° C. and CuCN (90 mg, 1 mmol) was added, followed immediately by the dropwise addition of diisopropyldichlorosilane (20.35 g, 0.11 mol). The reaction mixture was then allowed to warm to room temperature and stirred for 12 hours. The resultant mixture was filtered and the filtrate distilled to afford the desired silane (1)(14.5 g).

Synthesis of 2-(4-butenyldiisopropylsiloxy)indene (2)

To a solution of silane (1) (14.5 g, 73.2 mmol) and 2-indanone (9.7 g, 73.2 mmol) in benzene (30 ml) was added dropwise a solution of DBU (9 g, 73.2 mmol) in benzene (25 ml) at room temperature and the reaction mixture stirred for 12 hours. The mixture was then treated with water, extracted with diethyl ether, and the organic phase dried over sodium sulfate. After removal of the solvents under reduced pressure, purification by flash chromatography using hexane as eluent gave the desired indene (2) (12.9 g).

Synthesis of bis2-(4-butenyldiisopropylsiloxy)1-indenyl)ethane (3)

To a solution of indene (2) (12.9 g, 43.9 mmol) in THF (50 ml) was added dropwise n-butyllithium (19.7 ml of 2.5 M in hexane, 22 mmol) at −15° C. and the reaction mixture stirred for 2 hours at room temperature. To this solution was added dropwise 1,2-dibromoethane (4.5 g, 22 mmol) in THF (10 ml) at −78° C., and the reaction mixture was stirred for 12 hours at room temperature. The mixture was then poured into water, extracted with diethyl ether, the organic phase dried over sodium sulfate and the solvents removed under reduced pressure. Fractional distillation and flash chromatography using hexane as eluent gave the desired ethane (3) (2 g).

Synthesis of [Ethylenebis2-(4-butenyldiisopropylsiloxy)-1-indenyl)]zirconium dichloride (4)

To a solution of ethane (3) (2 g, 3.2 mmol) in diethyl ether (20 ml) was added dropwise n-butyllithium (2.4 ml of 2.5 M in hexane, 6.4 mmol) at −15° C. and the reaction mixture stirred for 2 hours at room temperature. The diethyl ether was then evaporated under reduced pressure to give a yellow powder to which $ZrCl_4$ (0.73 g, 3.2 mmol) was added. Cold dichloromethane (30 ml) was poured onto the mixture and the suspension was stirred at −80° C. for 15 minutes before being allowed to warm up slowly to room temperature. The reaction mixture was stirred for 12 hours. The suspension was filtered through Celite. The dichloromethane was then evaporated under reduced pressure. According to the NMR spectrum the solid obtained contained 44% of the desired dichloride (4) 0.5 g of which was isolated by recrystallisation in hexane at −78° C.

Synthesis of [bis(2-(4-butenyldiisopropylsiloxy)-indenyl)] zirconium dichloride (5)

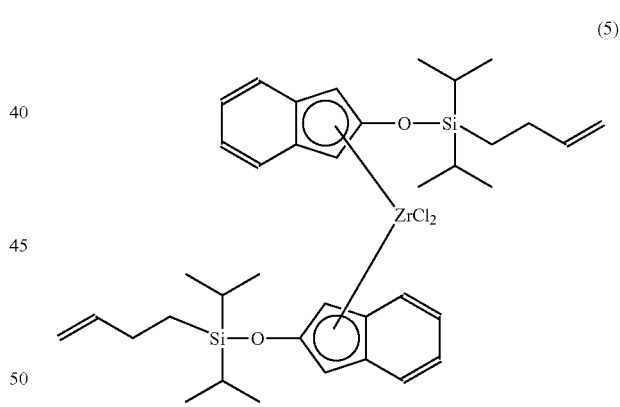

(5)

To a solution of indene (2) (1 g, 3.3 mmol) in diethyl ether (20 ml) at 0° C. was added dropwise n-butyllithium (1.3 ml of 2.5 M in hexane, 3.3 mmol). After complete addition, the reaction mixture was stirred for 2 hours at room temperature. The diethyl ether was evaporated under reduced pressure and $ZrCl_4$ (0.4 g, 1.65 mmol) was added to the resultant powder. After cooling the reaction mixture to −80° C., toluene (20 ml) was added. The suspension was then allowed to warm up slowly to room temperature and stirred for 12 hours. The solvent was evaporated under reduced pressure and dichloromethane added to the mixture and the resultant suspension filtered through Celite. Dichloromethane was removed under reduced pressure to give a yellow oil which contained, according to the NMR spectrum, 15% of the desired dichloride (5).

Rac-[dimethylsilylenebis (4-(4-butenyldiiso propylsiloxy)-1-indenyl)]zirconium dichloride (10)

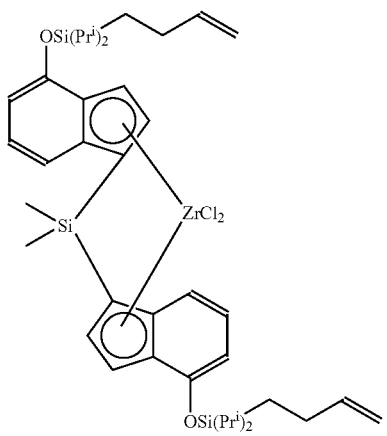

(10)

Synthesis of 4-(4-butenyldiisopropylsiloxy)-1-indanone (6)

To a solution of 4-hydroxy-1-indanone (9.85 g, 66.5 mmol) and triethylamine (8.9 g, 87.8 mmol) in dichloromethane (70 ml) at 0° C. was added dropwise a solution of the silane (1) (14.5 g, 73.2 mmol) in dichloromethane (20 ml). After complete addition, the reaction mixture was allowed to warm up to room temperature and was stirred for 12 hours.

The mixture was then treated with an aqueous solution of sodium hydrogencarbonate. The organic phase was separated, washed successively with water and brine then dried over sodium sulfate. After removal of the solvent under reduced pressure, purification by flash chromatography using hexane/ether (97:3) as eluent gave the desired indanone (6) (17.9 g).

Synthesis of 4-(4-butenyldiisopropylsiloxy)-1-indanol (7)

To a solution of indanone (6) (17.9 g, 56.64 mmol) in methanol/THF (1:2) (70 ml) at 0° C. was added sodium borohydride (3.26 g, 85.9 mmol) in portions. The reaction mixture was then allowed to warm up to room temperature and stirred for 12 hours.

The reaction mixture was then poured on to ice, acidified with concentrated hydrochloric acid to pH=1 and extracted with ether. The organic phase was washed with brine and water and dried over sodium sulfate. Removal of the solvents under reduced pressure gave the desired indanol (7) (17.5 g).

Synthesis of 4-(4-butenyldiisopropylsiloxy)indene (8)

To a solution of the indanol (7) (17.5 g, 55 mmol) in toluene (70 ml) was added oxalic acid (8.9 g, 99 mmol) and the mixture heated under reflux for 100 min.

After cooling down, the mixture was washed with a 10% aqueous solution of sodium hydrogencarbonate. The organic phase was then separated and dried over sodium sulfate. After removal of the solvent under reduced pressure, the purification by flash chromatography using hexane as eluent gave the desired indene (4) (7.5 g).

Synthesis of bis(4-(4-butenyldiisopropylsiloxy)-1-indenyl) dimethylsilane (9)

To a solution of indene (8) (7.5 g, 25 mmol) in THF (50 ml) at 0° C. was added dropwise n-butyllithium (10 ml of 2.5 M in hexane, 25 mmol). After complete addition, the reaction mixture was allowed to warm up to room temperature and was stirred for 2 hours. The solution was recooled 50 0° C. and dimethyldichlorosilane (1.6 g, 12.5 mmol) added dropwise. The reaction mixture was allowed to warm up to room temperature and was stirred for 12 hours.

The reaction mixture was then treated with water and extracted with ether, the organic phase dried over sodium sulfate and the solvents removed under reduced pressure. Fractional distillation and flash chromatography using hexane as eluent gave the desired silane (9) (3 g).

Synthesis of Rac-[dimethylsilylenebis(4-(4-butenyldiiso propylsiloxy)-1-indenyl)]zirconium dichloride (10)

To a solution of silane (9) (2.1 g, 3.2 mmol) in diethyl ether (20 ml) is added dropwise n-butyllithium (2.4 ml of 2.5 M in hexane, 6.4 mmol) at −15° C. and the reaction mixture stirred for 2 hours at room temperature. The diethyl ether is then evaporated under reduced pressure to give a yellow powder to which $ZrCl_4$ (0.73 g, 3.2 mmol) is added. Cold dichloromethane (30 ml) is poured onto the mixture and the suspension is stirred at −80° C. for 15 minutes before being allowed to warm up slowly to room temperature. The suspension is filtered through Celite and the dichloromethane then evaporated under reduced pressure. Analysis of the NMR spectrum indicates that the solid obtained contains the desired dichloride (10) which may be isolated by recrystallisation in hexane at −78° C.

Polymerization Reactions

Ethylene (>99.95%), nitrogen (>99.999%) and n-pentane (>97%) are used. 1-Hexene is purified by refluxing over sodium and distillation under an atmosphere of nitrogen.

Catalysts are prepared by mixing the co-catalyst (10 wt % or 30 wt % MAO in toluene or 70 wt % HIBAO in toluene, both from Albemarle) in toluene to reach the desired Aluminium: M (Metal) molar ratio.

PREPOLYMERISATION EXAMPLE

MAO (3.32 g) was measured by volume in a 10 ml vial and placed in a plastic syringe. Then metallocene 4, infra (38.2 μmol) was mixed with further MAO (3.32 g (measured by volume)) and placed in a burette.

To a stirred (400 $min^{-1}$) Büchi 1 L autoclave reactor was added (i) toluene (150 ml); (ii) the MAO contained in the plastic syringe; and, after a few minutes, (iii) the metallocene 4/MAO solution. The aluminium:zirconium ratio thus obtained was 300. The prepolymerisation was then conducted under an ethylene pressure of 0.3 bar at 20° C. for 2 h.

Polymerisation Example 1

The above reactor was then purged with nitrogen to remove ethylene and the reactor temperature adjusted to +80° C. The nitrogen pressure achieved during purging (pressure venting) was allowed to decrease and 2.85 bar of ethylene pressure was then applied. The polymerisation of ethylene was conducted for 30 min, maintaining ethylene pressure and temperature at a constant level. The consumption of ethylene was 0.7082 mol. The melting point of the polyethylene thus produced was determined to be 127° C.

Polymerisation Example 2

Polymerisation example 1 is repeated but after the prepolymersation is completed, the self-supported catalyst is

The invention claimed is:

1. A metallocene catalyst of formula (III):

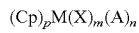

in which:
M is a transition metal ion or a lanthanide metal ion;
p is 1 or 2;
m is an integer greater than or equal to 0;
n is an integer greater than or equal to 0;
n+m is equal to the valency of the metal not satisfied by ligand or ligands Cp;
X is a ligand which co-ordinates to M;
A is a σ-ligand; and
each ligand Cp which may be the same or different is a $\eta^5$ cyclopentadienyl-containing ligand characterised in that at least one of Cp is directly or indirectly substituted by a pendant siloxy group of formula

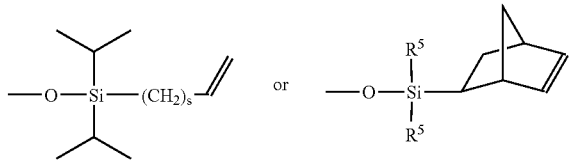

wherein s is 1 to 18 and each $R^5$ is independently selected from the group consisting of $C_{1-6}$ alkyl groups.

2. The catalyst as claimed in claim 1 wherein p is 2 and wherein all Cp ligands are directly or indirectly substituted by the pendant siloxy group of formula

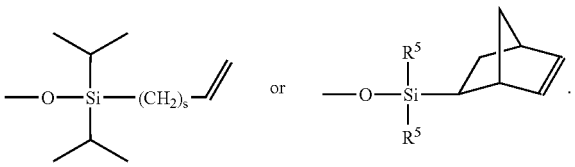

3. The catalyst as claimed in claim 1 wherein M is a group 4 to 6 transition metal.

4. The catalyst as claimed in claim 3, wherein M is Cr, Ti, Zr or Hf.

5. The catalyst as claimed in claim 1 wherein p=2 and m=0.

6. The catalyst as claimed in claim 1 wherein each A is independently selected from halo, amido or $C_{1-12}$-hydrocarbyl ligands.

7. The catalyst as claimed in claim 6 wherein each A is chloride.

8. The catalyst as claimed in claim 1 wherein $(Cp)_p$ is one or two ligands "Lig" wherein each Lig is independently a negatively charged cyclopentadienyl-containing moiety of the formulae (IVa) or (Va):

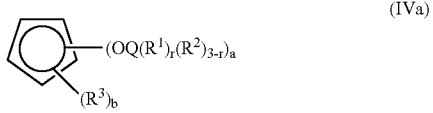

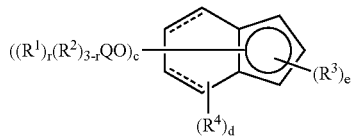

wherein one or more of the ring carbon atoms may be replaced by a ring heteroatom;
either or both of the bonds shown as --- in formula (Va) may be present or absent;
$—OQ(R^1)_r(R^2)_{3-r}$ represents

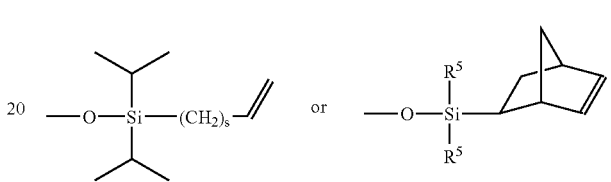

one or more groups of formula $—OQ(R^1)_r(R^2)_{3-r}$ is attached to either or both of the 5- or 6-membered rings shown, either directly or indirectly;
each $R^3$ or $R^4$ may be hydrogen or a group containing any of the atoms of group 14, 15 or 16 of the periodic table (IUPAC); optionally
two or more $R^3$ or $R^4$ groups attached to adjacent ring atoms on the same ring together form an optionally substituted 5- to 8-membered fused ring; and optionally one $R^3$ or $R^4$ is -L-Z wherein L is a 1 to 4 atom chain and Z is a second $\eta^5$-cyclopentadienyl containing moiety;
a is 1 to 4
b is 1 to 4
c is 1 to 4;
d is 1 to 4;
e is 1 to 3; the sum of a and b being no more than 5 and the sum of c, d and e being no more than 7;
with the proviso that no more than one -L-Z group is present in each ligand Lig.

9. The catalyst as claimed in claim 8 wherein Z is of formula (IVa) or (Va).

10. The catalyst of claim 8 wherein said one or more groups of formula $—OQ(R^1)_r(R^2)_{3-r}$ are attached directly to the 5-membered rings of formula (IVa) or (Va).

11. The catalyst of claim 8 wherein $R^3$ and $R^4$ are selected from $C_{1-20}$ hydrocarbyl, hydrocarbyl siloxy, hydrocarbyloxy, hydrocarbylgermyl-oxy, hydrocarbyl silyl or hydrocarbylgermyl group, or hydrogen.

12. The catalyst as claimed in claim 8 wherein Lig is a negatively charged indenyl or indenyloid moiety of formula (Va).

13. The catalyst of claim 12 wherein both of the bonds shown as — are present.

14. The catalyst of claim 12 wherein said substituent of formula $—OQ(R^1)_r(R^2)_{3-r}$ is present at the 2 or 4-position.

15. The catalyst of claim 12 wherein -L-Z is attached to the 5-membered ring.

16. The catalyst of claim 12 wherein -L-Z is attached at either of the 1- or 3-positions of the 5-membered ring shown.

17. The catalyst of claim 8 wherein all the ring atoms are carbon atoms.

18. The catalyst of claim 8 wherein L is of formula $(C(R^3)_2)_q$ on $Si(R^3)_2$ wherein q is 1 or 2 and $R^3$ is as defined in claim 8.

19. The catalyst of claim 18 wherein L is $CH_2$, $CH_2CH_2$ or $Si(CH_3)_2$.

20. The catalyst as claimed in claim 1 wherein s is 1 to 6.

21. The catalyst as claimed in claim 1 wherein both $R^5$ groups are the same.

22. The catalyst as claimed in claim 21 wherein both $R^5$ groups are isopropyl.

23. The catalyst as claimed in claim 8 wherein $(R^1)_r(R^2)_{3-r}$ QO is 4-butenyldiisopropylsiloxy.

24. The catalyst as claimed in claim 8 wherein only one $(R^1)_r(R^2)_{3-r}$ QO is present.

25. The catalyst as claimed in claim 8 wherein L-Z is absent.

26. The catalyst of claim 25 wherein a first Cp group is of formula (IVa) or (Va) and a second Cp group is a substituted (e.g. $C_{1-6}$-alkly substituted) or unsubstituted $\eta^5$-cyclopentadienyl containing ligand.

27. An olefin polymerisation catalyst system comprising or produced by the reaction of:
 (i) a metallocene catalyst as claimed in claim 1; and a cocatalyst/catalyst activator.

28. The olefin polymerisation catalyst system as claimed in claim 27 wherein said cocatalyst/catalyst activator is an aluminium alkyl compound.

29. A process for olefin polymerisation comprising polymerising an olefin in the presence of a metallocene catalyst as claimed in claim 1.

30. A ligand which consists of negatively charged cyclopentadienyl-containing moiety of formula (IVa) or (Va) as defined in claim 8.

31. A metallocene catalyst in which the metal is coordinated by an $\eta^5$ indenyl or indenyloid ligand wherein said ligand is directly or indirectly substituted at the 1,3,4 to 7 position by a pendant siloxy group which contains an olefinic residue.

* * * * *